United States Patent
Liebschner

(10) Patent No.: US 7,435,232 B2
(45) Date of Patent: Oct. 14, 2008

(54) NONINVASIVE TISSUE ASSESSMENT

(75) Inventor: Michael Liebschner, Pearland, TX (US)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 10/935,432

(22) Filed: Sep. 7, 2004

(65) Prior Publication Data

US 2005/0113691 A1    May 26, 2005

Related U.S. Application Data

(60) Provisional application No. 60/500,796, filed on Sep. 5, 2003, provisional application No. 60/553,670, filed on Mar. 16, 2004.

(51) Int. Cl.
*A61B 5/103* (2006.01)
*A61B 5/117* (2006.01)
*A61B 5/00* (2006.01)
*A61B 7/00* (2006.01)
*A61B 5/04* (2006.01)
*A61H 31/00* (2006.01)
*A61H 1/00* (2006.01)
*A61B 17/00* (2006.01)

(52) U.S. Cl. ............... 600/587; 600/552; 600/300; 600/301; 600/586; 600/372; 600/382; 600/384; 600/386; 128/920; 128/923; 601/46; 601/80; 606/201; 606/202

(58) Field of Classification Search ............... 600/552, 600/300, 301, 587, 586, 372, 382, 384, 386; 128/920, 923; 601/46, 80; 606/201, 202
See application file for complete search history.

(56) References Cited

U.S. PATENT DOCUMENTS 4,437,473 A    3/1984    Mollan (Continued)

FOREIGN PATENT DOCUMENTS

EP    0 786 232 A2    7/1997

(Continued)

OTHER PUBLICATIONS

Fellinger, M., et al., "Early detection of delayed union in lower leg fractures using a computerised analysis of mechanical vibration reactions of bone for assessing the state of fracture healing," Archives of Orthopaedic and Trauma Surgery, vol. 113 (1994), Springer-Verlag, pp. 93-96.

(Continued)

*Primary Examiner*—Max Hindenburg
*Assistant Examiner*—Jeffrey G Hoekstra
(74) *Attorney, Agent, or Firm*—Conley Rose, P.C.; Rodney B. Carroll

(57) ABSTRACT

Methods and apparatus for non-invasively assessing physiological hard of soft tissue of human and other species are described. In a preferred embodiment, tissue is vibrationally stimulated in vivo through a frequency spectrum. The tissue reacts against the stimulus and the reaction is preferably measured and recorded. Based on analytical algorithms or comparisons with previously taken measurements, changes within the tissue can be detected and used for diagnostic purposes. Further embodiments describe the usage of the device and methods for in vivo intra-operative and post-operative implant evaluations and as a therapeutic tool.

38 Claims, 8 Drawing Sheets

U.S. PATENT DOCUMENTS

| | | | |
|---|---|---|---|
| 4,574,763 A | | 3/1986 | Hallberg |
| 4,754,763 A | | 7/1988 | Doemland |
| 4,762,134 A | * | 8/1988 | Gala ........................... 600/594 |
| 4,947,851 A | * | 8/1990 | Sarvazyan et al. .......... 600/438 |
| 4,989,613 A | | 2/1991 | Finkenberg |
| 5,006,984 A | * | 4/1991 | Steele ......................... 600/587 |
| 5,024,239 A | | 6/1991 | Rosenstein |
| 5,368,044 A | | 11/1994 | Cain et al. |
| 5,402,781 A | | 4/1995 | Dimarogonas |
| 5,413,116 A | | 5/1995 | Radke et al. |
| 5,458,119 A | | 10/1995 | Vanharanta |
| 5,533,519 A | | 7/1996 | Radke et al. |
| 5,549,544 A | | 8/1996 | Young et al. |
| 5,614,674 A | | 3/1997 | Dimarogonas |
| 5,630,422 A | | 5/1997 | Zanakis |
| 5,652,386 A | | 7/1997 | Dimarogonas |
| 5,656,017 A | | 8/1997 | Keller et al. |
| 5,766,137 A | * | 6/1998 | Omata ........................ 600/587 |
| 5,836,876 A | | 11/1998 | Dimarogonas |
| 5,895,357 A | | 4/1999 | Ohtomo |
| 5,895,364 A | | 4/1999 | Donskoy |
| 5,897,510 A | * | 4/1999 | Keller et al. ................. 600/594 |
| 5,938,610 A | | 8/1999 | Ohtomo |
| 6,024,711 A | | 2/2000 | Lentle et al. |
| 6,095,979 A | | 8/2000 | Ohtomo |
| 6,117,089 A | | 9/2000 | Sinha |
| 6,234,975 B1 | | 5/2001 | McLeod et al. |
| 6,371,916 B1 | * | 4/2002 | Buhler et al. ................ 600/449 |
| 6,565,520 B1 | | 5/2003 | Young |
| 6,569,098 B2 | * | 5/2003 | Kawchuk ..................... 600/587 |
| 6,584,450 B1 | | 6/2003 | Hastings et al. |

FOREIGN PATENT DOCUMENTS

| | | |
|---|---|---|
| EP | 0 687 163 B1 | 8/2000 |
| EP | 1 232 727 A2 | 8/2002 |
| WO | WO 94/20024 | 9/1994 |
| WO | WO 99/07280 | 2/1999 |
| WO | WO 00/31371 | 8/2000 |
| WO | WO 01/19248 A1 | 3/2001 |

OTHER PUBLICATIONS

Flint, et al., "Determination of Fracture Healing By Transverse Vibration Measurement: A Preliminary Report," (1994), Taylor & Francls Ltd., pp. 205-207.

Georgiou, A.P., et al., "Accurate diagnosis of hip prosthesis loosening using a vibrational technique," Clinical Biomechanics, vol. 16, (2001), Elsevier Science Ltd., pp. 315-323.

Griffin, Michael J., et al., "The diagnosis of disorders caused by hand-transmitted vibration: Southampton Workshop 2000," International Archives of Occupational and Environmental Health, Appendix X5B to Final Report (May 2001), EC Biomed II concerted action BMH4-CT98-3291, pp. 1-15.

Hayami, et al., "Shock Absorbing Ability of Joint Materials: I. Development of Noncontact Type Ninstrument Using Acoustic Loading Vibration For Determining The Loss Factor Of Human Joint Tissues," Seitai Zairyo, vol. 10, Issue 6 (1992), pp. 311-318.

Hobatho, M.C., et al., "Vibration Mode Testing of the Human Tibia In Vivo," Archives Internationales de Physiologie, de Biochemie et de Biophysique, vol. 102, Issue 3 (1994), pp. C67-C68.

Horn, Terry S., "The Identification Of Cortical Microdamage In Fatigue-Loaded Bone Using A Non-Invasive Impulse Response Vibration Testing Technique," Bone, vol. 14, (1993), Pergamon Press Ltd., USA, pp. 259-264.

Jurist, John M., Ph.D., "In Vivo Determination of the Elastic Response of Bone: I. Method of Ulnar Resonant Frequency Determination," Phys. Med. Biol., vol. 15, No. 3 (1970), pp. 417-426.

Jurist, John M., Ph.D., "In Vivo Determination of the Elastic Response of Bone: II. Ulnar Resonant Frequency in Osteoporotic, Diabetic and Normal Subjects," Phys. Med. Biol., vol. 15, No. 3 (1970), pp. 427-434.

Kanai, H., et al., "In vivo measurement of frequency characteristics of phase velocity of bone with bending vibration," Electronics Letters, vol. 31, No. 23 (Nov. 1995), pp. 1969-1971.

Kernohan, George W., Ph.D., et al., "The Diagnostic Potential of Vibration Arthrography," Clinical Orthopedics and Related Research, No. 210 (Sep. 1986), pp. 106-112.

Krishnan, S., et al., "Adaptive filtering, modelling and classification of knee joint vibroarthrographic signals for non-invasive diagnosis of articular pathology," Medical & Biological Engineering & Computing, vol. 35 (Nov. 1997), pp. 677-684.

Krishnan, Sridhar, et al., "Adaptive Time-Frequency Analysis of Knee Joint Vibroarthrographic Signals for Noninvasive Screening of Articular Cartilage Pathology," IEEE Transactions on Biomedical Engineering, vol. 47, No. 6 (Jun. 2000), IEEE, pp. 773-783.

Kirshnan, Sridhar, et al., "Sonification of Knee-joint Vibration Signals," Proceedings of the 22nd Annual EMBS International Conference, Jul. 23-28, 2000, Chicago, IL, IEEE, pp. 1995-1998.

Krishnan, Sridhar, et al., "Auditory display of knee-joint vibration signals," Journal of the Acoustic Society of America, vol. 110, No. 6 (Dec. 2001), Acoustical Society of America, pp. 3292-3304.

Li, P.L.S., et al., "Loosening Of Total Hip Arthroplasty: Diagnosis By Vibration Analysis," The Journal Of Bone And Joint Surgery, vol. 77-B, No. 4, (Jul. 1995), pp. 640-644.

Liu, et al., "Vibration Arthrography Of The Knee Joint Disorders," Biomed. Eng. Appl. Basis Commun., vol. 5, No. 1 (1993), pp. 53-60.

McCoy, Gerald F., et al., "Vibration Arthrography As A Diagnostic Aid In Diseases Of The Knee: A Preliminary Report," The Journal of Bone And Joint Surgery, vol. 69-B, No. 2 (Mar. 1987), British Editorial Society of Bone and Joint Surgery, pp. 288-293.

McCrea, et al., "Vibration Arthrography in The Diagnosis of Knee Joint Diseases," Z Orthop., vol. 123, No. 1 (Jan.-Feb. 1985), pp. 18-22+abstract.

Moussavi, Zahra M.K., et al., "Screening of Vibroarthrographic Signals via Adaptive Segmentation and Linear Prediation Modeling," IEEE Transactions On Biomedical Engineering, vol. 43, No. 1, (Jan. 1996), pp. 15-23.

Reddy, Narender, P., et al., "Noninvasive Acceleration Measurements to Characterize Knee Arthritis and Chondromalacia," Annals of Biomedical Enginnering, vol. 23 (1995), Biomedical Engineering Society, USA, pp. 78-84.

Roberts, S.G., "Noninvasive Determination Of Bone Mechanical Properties Using Vibration Response: A Refined Model and Validation In Vivo," Journal of Biomechanics, vol. 29, No. 1 (1996), Elsevier Science Ltd., pp. 91-98.

Shen Y., et al., "Localization of knee joint cartilage pathology by multichannel vibroarthrography," Medical Engineering & Physics, vol. 17, No. 8 (1995), Elsevier Science Ltd. for BES, Great Britain, p. 583-594.

Tavathia, Sanjeev, et al., "Analysis of Knee Vibration Signals Using Linear Prediction," IEEE Transactions on Biomedical Engineering, vol. 39, No. 9 (Sep. 1992), IEEE, pp. 959-970.

Willinger, et al., "In Vivo Determination of Long Bone Flexibility—The Epiphyses Influence," Biomed. Sci. Instrum., vol. 26, (1990), pp. 45-47.

Foreign communication from a counterpart application—International Search Report and Written Opinion, PCT/US04/28990, Mar. 29, 2006, 8 pages.

El-Baly, T. H., et al., "Vibratory coherence as an alternative to radiography in assessing bone healing after osteodistraction," Annals of Biomedical Engineering, 2002, pp. 226-231, vol. 30, Biomedical Engineering Society.

* cited by examiner

NONINVASIVE TISSUE ASSESSMENT

CROSS-REFERENCE TO RELATED APPLICATIONS

The present application claims the benefit of 35 U.S.C. 111(b) U.S. Provisional Application Ser. No. 60/500,796 filed Sep. 5, 2003, entitled "Noninvasive Bone and Joint Damage Detection Device" and U.S. Provisional Application Ser. No. 60/553,670 filed Mar. 16, 2004, which are hereby incorporated by reference herein for all purposes.

STATEMENT REGARDING FEDERALLY SPONSORED RESEARCH OR DEVELOPMENT

None

FIELD OF THE INVENTION

The present invention relates to a method and apparatus for in-vivo investigation and characterization of tissue. In particular, the present invention relates to the use of vibration for assessment of tissue.

BACKGROUND OF THE INVENTION

The investigation of the mechanical properties of bone in vivo is of great interest in view of the occurrence of fracture risk in osteopenia or osteoporosis. Osteoporosis may be defined as a metabolic disease causing an unbalance in the natural process of bone resorption and bone formation with the result of a loss of mechanical strength and increased risk of fractures. The degradation of the mechanical strength of the bones may proceed to a stage where even minimal trauma results in bone fractures. Osteoporosis affects more than 20 million people in the U.S. and causes 1.5 million fractures each year. Although age-related bone loss occurs in both men and women, it begins earlier and progresses more rapidly in women. It is estimated that osteoporosis affects about 45 percent of all postmenopausal white women.

An accurate assessment of osteoporosis is difficult. The bones in the skeleton are by nature non-homogeneous and different parts of the skeleton may not be affected to the same degree. The material strength of the bones naturally changes over time, reaching a maximum about the age from 20-30 years and gradually declining later on. Individual differences may be substantial. Treatments do exist which may delay or reverse the progression of osteoporosis. These treatments are most effective when a patient can be diagnosed at an early stage.

The existing technology for predicting fracture risk and osteoporosis often exposes the patient to cumulative doses of X-rays, including, for example, plain X-rays and dual-energy X-ray absorptiometry (DEXA). The risk of long-term effects from X-ray radiation is compounded by multiple exposures whenever the patient is to be reevaluated. Typical X-ray scanners are very expensive and require extensively trained technicians to operate. In addition, the expense and/or inconvenience of existing technology that can only be accessed with an office visit is not conducive to early detection because it limits the number of times a patient will actually be checked. Being tested only every other year or less for the early stages of osteoporosis may not be enough. Studies have shown that in some cases a patient can experience bone loss of up to 10% in a 12 month period. Further, the existing technology may report only bone areal density, and do not directly indicate bone strength or tendency for bone loss, nor do they take into account differences in body build, body weight, patient height, or loading history. In addition, by ignoring bone volume, it is entirely possible that one small vertebra of normal density and another much larger but osteoporotic vertebra will yield the same reading.

Another method of diagnosing osteoporosis is to estimate bone mass through ultrasound velocity measurements. Unfortunately, these tests are limited to bones, such as the calcaneus and patella, which suffer from osteoporosis to a negligible extent and are only weakly indicative of risk of fracture. Traditional bone mass measurements, by their very nature, are unable to predict bone loss prior to its occurrence and can only chart the course of bone loss over an extended period of time. Further, these diagnostics only consider bone mass, and fall to consider bone integrity and other factors such as tendency to fall, or ability to protect oneself during falling. In addition, the capital expense associated with this type of technology can be greater than $7,500.

Because it is desirable to institute treatment for osteoporosis early on, a need exists for an inexpensive, convenient, non-invasive technique for diagnosing fractures and/or osteoporosis in its early stages. The following disclosure may address one or more of these issues.

SUMMARY OF THE INVENTION

The present invention relates to methods and apparatus for non-invasively detecting tissue damage, e.g., fractures and/or bone loss. Possible tissues for use with the present invention include both hard and soft tissues.

In general, tissue is vibrationally stimulated in vivo through a frequency spectrum. The tissue reacts against the stimulus and the reaction is measured and preferably recorded. Based on previously taken measurements of the patient or other patients, deficiencies within the tissue can be detected and used for diagnostic purposes.

In one embodiment, a device for tissue assessment comprises a signal generator capable of generating a signal, a means for converting the signal into a vibration over a frequency range into one or more tissues at a designated point on a patient's body, and a means for measuring a tissue response at that same point on the patient's body. The device is capable of housing all of the necessary components within a single original device. Other embodiments of the device include a vibration generator that uses one or more piezoelectrical, electromagnetic, electromechanical, pneumatic and hydraulic actuators.

In another embodiment of the invention, a method for assessing tissue comprises generating a vibration over a frequency range (preferably about 20 Hz to about 1.5 MHz) based on a given set of operational parameters. The parameters may include, among other things, the anatomical site being tested, as well as the age and sex of the patient being tested. The generated vibration is transferred into one or more tissues (generally comprising both hard and soft tissue) at a desired anatomic region (preferably near a bone having only a thin layer of soft tissue) once a load has been applied to the anatomic region. The vibration or frequency sweep can by applied automatically or manually when the appropriate load is achieved. The vibration is transferred to the tissue, which generates a response and is measured. The data collected can be used to calculate a user response to provide the patient with a diagnosis.

In another embodiment of the invention, a device (as described herein) is pressed against the skin in an anatomic region with a relatively thin flesh layer. Choosing such a region will reduce measurement errors due to the interaction between soft and hard tissue. Measurement methodologies presented herein are intended to circumvent this problem. Constant contact pressure is either monitored through a mechanical constant spring system or via a software and load-cell system. A mechanical or software trigger mechanism starts the testing procedure when adequate pressure is applied. The test will run for a duration of about 1 to about 30 seconds, preferably about 5 seconds. Preliminary data analysis calculating signal to noise ratio and signal strength will indicate if the test will need to be repeated. The time signals from the electromagnetic shaker (driver), the accelerometer (output) and the load cell (input) will be recorded and at a given time transferred to a computer or microprocessor for analysis.

In yet another embodiment of the invention, a method for diagnosing tissue quality comprises generating a relative value by inducing a vibration (frequency sweep) into an anatomic region and measuring the region's response. The relative value may be compared with one or more previous values generated for the same patient. The values being stored on the device or a remote computer. Alternatively, the relative value may be compared with data from a database or look-up table. The database or look-up table may be contained on a computer wherein the database is updated via subscription service to an active collection and/or storage station. In still a further embodiment, the relative value may be transmitted via the internet or other communication to a remote database for comparison with other similar values calculated from the same or other patients having known tissue characteristics. A comparative value or diagnosis may be created and communicated back to the user.

These and other embodiments of the present invention, as well as their features and advantages, will become apparent with reference to the following detailed description.

BRIEF DESCRIPTION OF THE DRAWINGS

A better understanding of the present invention can be obtained when the following detailed description of the preferred embodiment is considered in conjunction with the following drawings, in which.

NOTATION AND NOMENCLATURE

Figure 1:
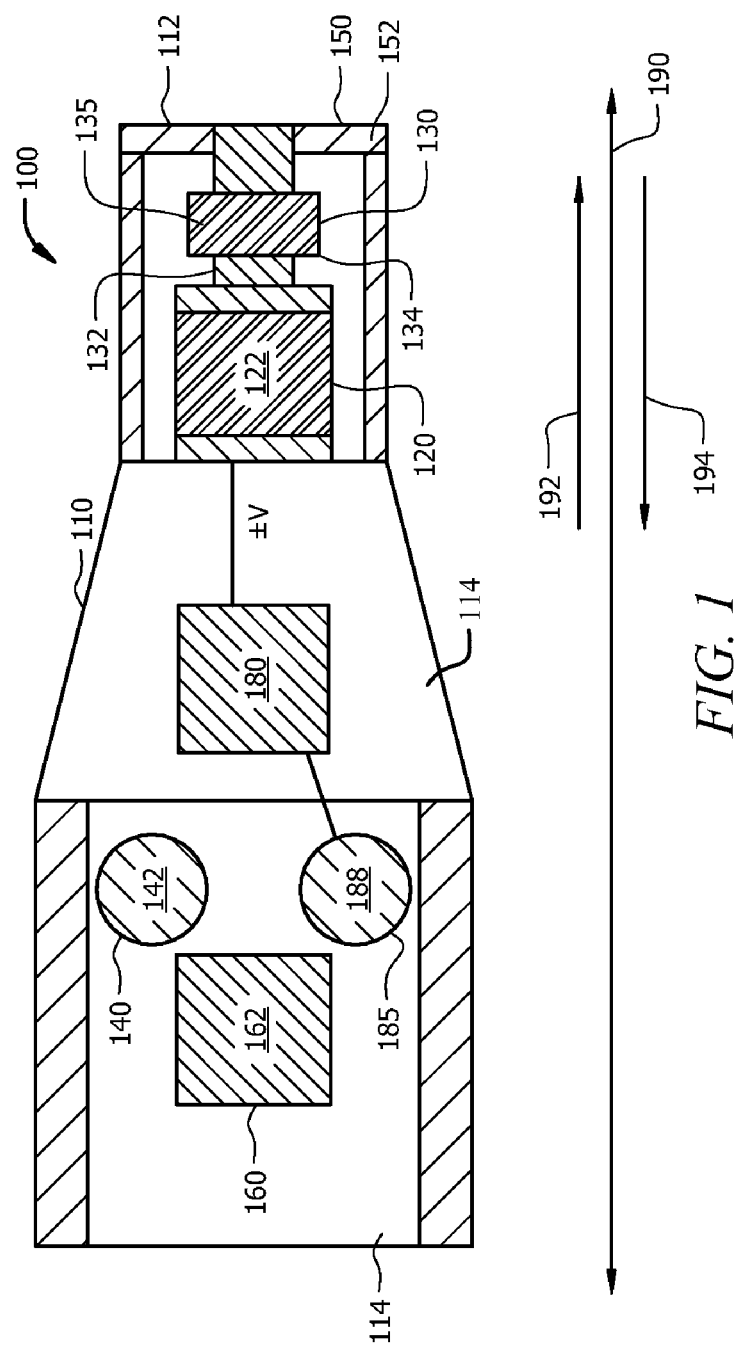
FIG. 1 shows one embodiment of a portable tissue characterization device in accordance with one or more principles of the present invention.

In the following discussion and in the claims, the term "hard tissue" is intended to encompass tissues such as bone or the like. Similarly, the term "soft tissue" is intended to encompass tissues such as cartilage, tendon, ligaments, skin, fat muscle, or the like. It will be understood that within the category of hard tissues, the tissues will have varying degrees of hardness (e.g. bone is harder than cartilage). Consequently, a subset of hard tissues includes bone and "joint tissues", where the term "joint tissue" is intended to encompass any hard tissue other than bone. Also, as used herein, the term osteopenia refers to any decrease in bone mass below the normal, and includes such conditions as osteoporosis.

DESCRIPTION OF THE INVENTION

As can be appreciated, osteopenia and osteoporosis, i.e., the loss of bone mass, arises to a large degree from the natural aging process, but also to a lesser degree from a decrease in muscle activity, such as due to bed rest. This loss can be detected using vibrational stimulation arising from a source external to the body, which creates mechanical, frequency specific, low level oscillations in the subjacent bones. Compared to imaging techniques such as DXA that neglect the volume of the measured bones, or ultrasonometer that measure localized speed of sound, acoustic vibrations around the natural frequency of an object excite the whole object, independent of size and shape. Changes in shape and bone mass content will alter its responsive frequency, and can thus be detected by the disclosed device and/or using the disclosed methods.

In more technical terms if one considers trabecular bone as a random network of struts, it is known from percolation theory that when a fraction $v_o$ of struts are randomly removed from a large network, it will spontaneously fragment into multiple segments. The strength of the network, as a whole, will vanish at that point. The value (at which fragmentation occurs) $v_o$, known as the bond-percolation threshold, depends on the class of networks being evaluated. For three dimensional Voronoi structures (structures assuming a random network of struts) its value is $v_0=0.5$. Thus, when half the struts on a Voronoi network are randomly removed, its fracture load (strength) vanishes. Because trabecular perforation has been shown to be the dominant cause of bone damage, it can be expected that the fracture load of trabecular bone will vanish when it loses about half its mass. Consequently, the commonly used power-law relationship (regression fit that correlates fracture load with bone mineral density) between fracture load and density of bone (Bell, G. H., O. Dunbar, et al. (1967). "Variations in strength of vertebrae with age and their relation to osteoporosis." *Calcified Tissue Research* 1(1): 75-86); McElhaney, J. H., J. L. Fogle, et al. (1970). "Mechanical properties on cranial bone." *J Biomech* 3(5): 495-511; Carter, D. R. and W. C. Hayes (1977). "The compressive behavior of bone as a two-phase porous structure." *Journal of Bone and Joint Surgery* 59-A: 954-962; McBroom, R. J., W. C. Hayes, et al. (1985). "Prediction of vertebral body compressive fracture using quantitative computed tomography." *J Bone Joint Surg Am* 67(8): 1206-14; Rice, J. C., S. C. Cowin, et al. (1988). "On the dependence of the elasticity and strength of cancellous bone on apparent density." *Journal of Biomechanics* 21(2): 155-168)—all references listed above are hereby incorporated by reference.) can only be an approximation that is invalid for weak bones; because under a power-law both the strength and density will vanish simultaneously. The power-law relationship does not take into account the spatial organization of the trabecular tissue.

Accordingly, an estimate of the percolation threshold $v_0$ for trabecular bone at different anatomic sites is a need that still exists in the art, because trabecular bone resembles disordered cubic networks more closely than Voronoi networks. Mosekilde, L. (1988). "Age-related changes in vertebral trabecular bone architecture—assessed by a new method." *Bone* 9(4): 247-50. In accordance with the present invention, a method for detecting osteopenia and osteoporosis comprises the step of inducing a relatively low level deformation in the bone tissue within a relatively large frequency range, preferably by mechanically loading the bone.

The present invention includes both apparatus and methods for testing or characterizing tissue, particularly bone. Certain embodiments also include using the apparatus described herein as a therapeutic tool, particularly in the area of chiropractics, pain relieve, bone growth stimulation, bone healing (particularly after surgery) and osteoporosis treatment at selected anatomic sites. In reconstructive surgery, requiring implants, the present invention can be utilized as an intra-operative and post-operative diagnostic tool to evaluate implant fixation and implant loosening over time. Such embodiments generally comprise finding the natural frequency for a specified tissue in order to induce the maximum excitation of the tissue. Other embodiments include business methods of using the devices and methods described herein as a means for generating a diagnostic database and generating a revenue stream based on subscriptions or access to diagnostic data.

In general, the apparatus embodiments for tissue quality assessment comprise a signal generator capable of generating a signal, a means for converting the signal into a vibration over a frequency range into one or more tissues at a designated point on a patient's body, and a means for measuring a tissue response at that same point on the patient's body. The device is capable of housing all of the necessary components within a single original device. The device should be capable of inducing a vibration over the frequency range of about 20 Hz to about 1.5 MHz. The vibration generation may normally comprise a shaker having one or more devices selected from the group consisting of a piezoelectric device, an electromagnetic device, an electromechanical device, a pneumatic device and a hydraulic device. The means for measuring a tissue response comprises an impedance transducer, which may comprise one or more selected from the group consisting of an accelerometer, a displacement transducer and a load cell. Further, the impedance transducer in certain embodiments is capable of measuring an input and output signal. Other components are contemplated for various embodiments as would be understood by one of ordinary skill in the art such as power amplifiers, signal converters, data storage, power sources, data transmitters, input and output components, and the like.

Other embodiments comprise one or more additional portable and/or remote sensors for measuring localized tissue damage. Each remote sensor should be capable of measuring the tissue response at a different region from the primary vibration point of origin using one or more accelerometer, load cell and/or a displacement transducer. One advantage to the present invention is that tissue can be evaluated without the need for stabilizers and/or the use of the 3 point testing procedure, which is typical in determining bone stiffness.

Referring now to FIG. 1, a tissue characterization device 100 is shown. Tissue characterization device 100 includes a housing 110, an actuator 120, an accelerometer 130, and a data acquisition system 160. Actuator 120 and accelerometer 130 are preferably located within housing 110. Data acquisition system 160 may be located within housing 110 or may be external to housing 110. In some embodiments, tissue characterization device 100 further includes a tissue contact pressure sensor 150 located on the proximal end 112 of housing 110.

Housing 110 may be constructed of any suitable material or materials. Additionally, housing 110 may be a continuous piece (not shown) or shaped into a plurality of modules 114. Housing 110 preferably encloses the components of tissue characterization device 100 such that tissue characterization device 100 is a self-contained assembly. For example, in some embodiments, tissue characterization device 100 may additionally include a power means (not shown), such as a battery, so that tissue characterization device 100 is freely mobile, ie. cordless.

Actuator 120 preferably comprises a piezoelectric element 122. When mechanical load is applied to a piezoelectric element, the piezoelectric element generates electric charge separation, resulting in electric field or voltage. Conversely, when an electric field or voltage is applied to a piezoelectric element, the piezoelectric element undergoes a mechanical deformation.

In some embodiments, piezoelectric element 122 consists of a plurality of thin layers (not shown) of electroactive ceramic material electrically connected in parallel. The total displacement $D_T$ piezoelectric element 122 moves is the sum of the displacements $D_i$ of the individual layers. The thickness $T_i$ of each individual layer determines the maximum operating voltage for actuator 120. Suitable piezoelectric materials include, for example, quartz, tourmaline, Rochelle salt, barium titanate, and lead zirconate titanate (PZT).

In some embodiments, piezoelectric element 122 may be replaced with an acoustic actuator (now shown). Acoustic actuators may be desirable in some instances, such as those where a load-controlled device is required.

Data acquisition system 160 preferably includes a data logger 162. In some embodiments, data logger 162 records data or measurements made by tissue characterization device 100. In other embodiments, data logger 162 records and manipulates data. In still other embodiments, data logger 162 records and manipulates data and presents results. Data logger 162 may transfer data, manipulated data, and/or results to a computer (not shown), e.g. via a wireless connection or cable.

In a preferred embodiment, an internal control and/or measurement unit 180 applies a positive voltage (+) across piezoelectric element 122. In response, piezoelectric element 122 mechanically deforms and forces a piston 132 and accelerometer 130 to move along x-axis 190, as indicated by arrow 192. In addition to piston 132, accelerometer 130 additionally includes a load cell 134 connected to piston 132. Load cell 134 preferably comprises a weight element 135.

When the voltage across piezoelectric element 122 is kept at its current value, piezoelectric element 122 remains in its most recent position. In order to deform piezoelectric element 122 in the opposite direction, measurement unit 180 applies an inverse or negative voltage (−) across piezoelectric element 122. This allows piston 132 to move back toward its original position along x-axis 190, as indicated by arrow 194. Preferably, the voltage is an alternating voltage, such that piezoelectric element 122 is continuously changing between its original and deformed shapes. This in turn, causes piston 132 to move back and forth along x-axis 190 at a variable piston frequency and magnitude. Applying an offset voltage can change the motion profile from oscillation to pulsation.

As stated above, a pressure sensor 150 may be located on the proximal end 112 of housing 110. Pressure sensor 150 preferably comprises a compressible pad 152 such that upon contact with a patient's body (not shown), pressure sensor 150 compresses accordingly. When a pressure sensor 150 is present, pressure sensor 150 is preferably in communication with internal control unit 180. Internal control unit 180 is capable of receiving pressure sensor data from pressure sensor 150 and indicating adequate pressure levels for taking repeatable measurements.

When pressure sensor 150 is not present, tissue characterization device 100 may have a power control means 140 that is in communication with internal control unit 180. In some embodiments, power control means 140 is a knob or wheel 142 such that at a first position (not shown) tissue characterization device 100 is "off" and when power wheel 142 is turned clockwise to a second position (not shown), tissue characterization device is "on." Power control means 140 is preferably located at least partially external to housing 110 such that a user may physically access it. In a preferred embodiment, tissue characterization device 100 is configured such that the amount a user turns power wheel 142 counterclockwise corresponds to the voltage magnitude being sent to piezoelectric element 122. It has been contemplated that internal control unit 180 has a number of predetermined settings (i.e. frequencies and magnitudes), which may correspond to visual marking on power wheel 142. For example, power wheel 142 may have a "0" or "off" marking (not shown) to let the user know tissue characterization device 100 is off. Power wheel 142 may additionally have markings, for example from 1-10 (not shown), to let the user know that tissue characterization device 100 is on and that there are different settings that tissue characterization device 100 can operate at (i.e. different settings according to chosen anatomic sites—femur, tibia, spine, and others).

Regardless of the mechanism for turning tissue characterization device 100 on, tissue characterization device 100 also preferably comprises an emergency off means 185. In a preferred embodiment, emergency off means 185 comprises a feedback loop (not shown) within or in communication with internal control unit 180. The feedback loop preferably monitors the amount of load placed on actuator 120, and if the load/pressure exceeds a predetermined threshold, the feedback loop forces or instructs internal control unit 180 to stop sending voltage to piezoelectric element 122. In other embodiments, emergency off means 185 comprises a button 188 located at least partially external to housing 110 so that a user may easily access it. Similar to feedback loop 186, button 188 is in communication with internal control unit 180 and forces or instructs internal control unit 180 to stop sending voltage to piezoelectric element 122 when button 188 is pushed.

As described above, piston 132 moves back and forth along x-axis 190 at a variable piston frequency and magnitude. The piston frequency and magnitude directly correspond to the voltage frequency and magnitude applied to piezoelectric element 122. As can be appreciated, piston 132 is the portion of tissue characterization device 100 that contacts a patient's body and applies a mechanical deformation to an anatomical region of the patient's body. Therefore, the piston frequency and magnitude also directly correspond to the patient contact frequency and magnitude.

The frequency range of the mechanical stimulus applied to the patient's body or tissue is generally between about 1 hertz and 1 megahertz, preferably between about 20 hertz and about 600 kilohertz and is more preferably between about 100 and about 600 hertz. The magnitude of the deformation induced in the tissue is preferably between about 0.1 and about 5 millimeters and is more preferably between about 0.5 and about 2 millimeters at the above-mentioned frequency ranges. The optimal frequency of the mechanical deformation is between about 100 Hertz and about 600 hertz, and the optimal peak-to-peak level of the deformation induced in the tissue is about 0.5 millimeter at the optimal frequency range. The optimal contact load applied to the patient through tissue characterization device 100 and monitored with pressure sensor 150 is in the range of about 10 Newtons to about 20 Newtons. However, the contact load need only be maintained at a range between 10 Newtons and 100 Newtons to result in a valid test. In a preferred embodiment, a stepwise frequency "sweep" is applied to the patient from about 20 Hz to about 1.5 MHz, preferably about 20 Hz to about 600 kHz.

Figure 2:
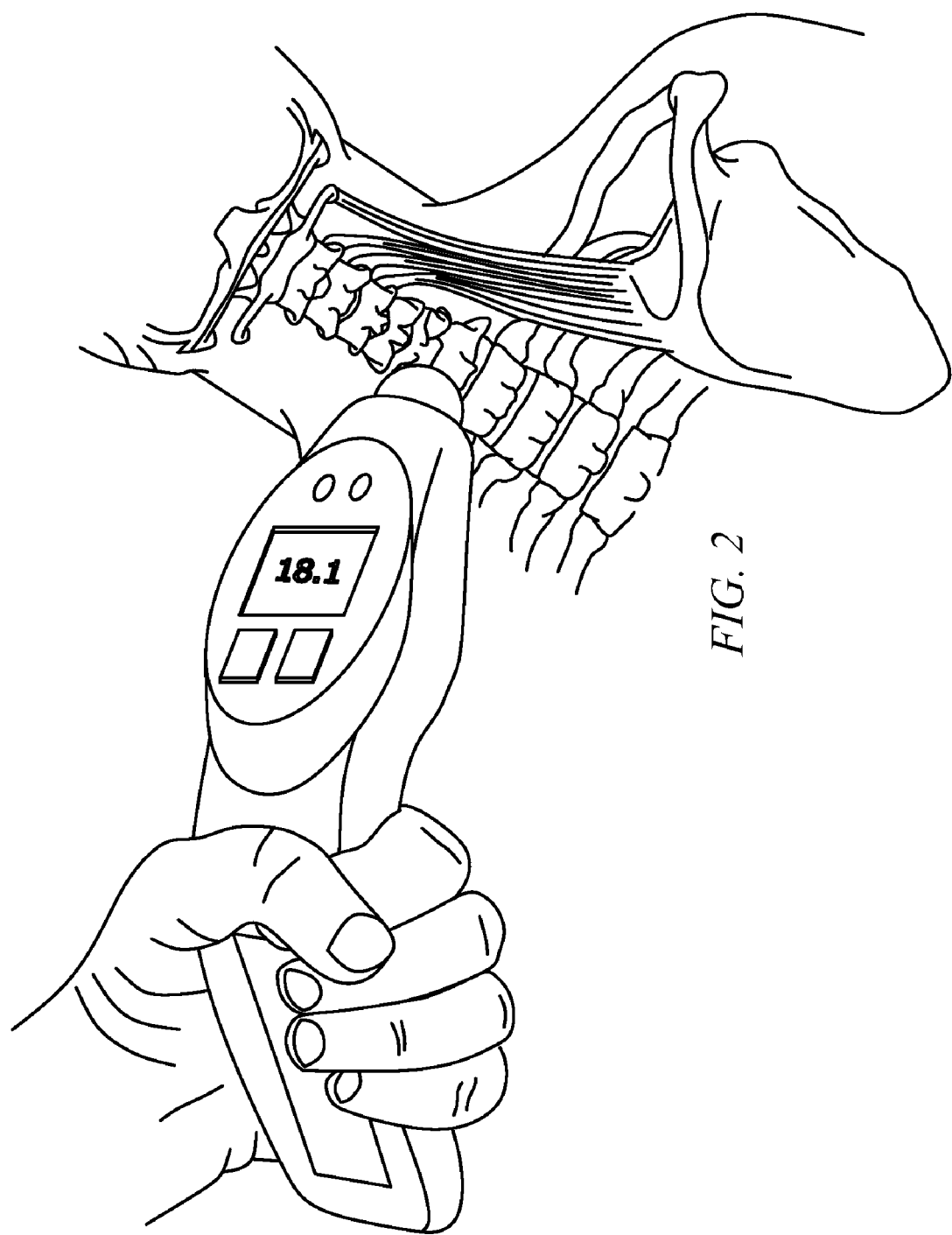
FIG. 2 shows an illustration of a tissue characterization device placed in contact with a patient's body in accordance with one or more principles of the present invention.

In a preferred embodiment, piston 132 or pressure sensor 150 of tissue characterization device 100 is placed in contact with a patient's body at a particular location, e.g. spine (FIG. 2). Upon contact with the patient's body, pressure sensor 150 sends a signal to internal control unit 180, which turns tissue characterization device 100 on. In the on mode, internal control unit 180 applies a voltage to the actuator, preferably piezoelectric element 122, at a predetermined frequency and magnitude. This causes piston 132 to oscillate back and forth, generating a mechanical deformation on the patient's local anatomical tissue at a specific frequency. Data logger 162 then records the body's response to the mechanical deformation by measuring the output signal from the load cell and accelerometer as a function of frequency. The data logger is an off-the-shelf device driven by a microprocessor. An internal algorithm transforms the data preferably using Fast-Fourier-Transformation and determines the peak response of the tissue versus frequency. These preliminary data will be used to determine the validity of the test, which is indicated on the display 311.

In some embodiments, tissue characterization device 100 is used to characterize hard tissues including bone and joint tissues. Bone and joint tissues generate different responses from each other when a mechanical stimulus is applied to them. The present inventor has discovered that by applying a frequency sweep to the hard and soft tissues, the different responses can be separated from the complex tissue response. In a preferred embodiment, the frequency spectrum indicates the damping factor of the tissues. This enables a user to characterize multiple tissues, such as articular cartilage and the surrounding bone simultaneously.

It has been contemplated that in order to determine changes within tissues such as bone and joint tissues, data sets could be used. These data sets may be established in a laboratory, i.e. in vitro testing and simulation of different injury mechanism, or be a previously recorded data set of a patient. When the data set comprises a previously recorded data set of a patient, the progress of a patient may be monitored. This is especially useful in osteoporotic patients, for which imaging techniques such as computerized tomography (CT) do not have the necessary resolution and are too expensive to repeat at every physical exam.

The present invention overcomes the inherent disadvantages of conventional bone quality assessment tools. It is less dangerous and more easily applied to the patient, especially the elderly. The low level of the mechanical deformation minimizes the chance of injury to the patient and the bone tissue being characterized, and the relatively high frequency range of loading significantly reduces the period of time required for such mechanical exposure. Finally, it would appear that bone and joint tissue is acutely responsive to stimuli induced in the above-mentioned frequency ranges, thereby having a therapeutic effect.

In addition to characterizing hard tissues and joints, it has been contemplated that the present invention may be used to characterize other tissues including skin and lymphoid tissue. For example, the present invention may be used to detect abnormalities in both of these tissues such as melanomas.

The same technique described above to characterize hard or soft tissue non-invasively can alternately be used to evaluate the stability of foreign implants in the body, such as fracture fixation devices, as well as monitor wound healing. In characterizing the dynamic response of patients implants in load-bearing anatomic sites the present invention can be utilized to monitor implant longevity. Furthermore, during surgery, the pre-load generally applied on bone-implant constructs may be monitored and used as an indicator for adequate adjustment of the implant. Additionally, during minimally invasive procedures such as a vertebroplasty or kyphoplasty, tissue characterization device 100 may be used to monitor the effectiveness of the treatment during operation before the patient applies his own weight onto the bone. Corrections of the surgical approach while the patient is still in the operating room are feasible using the present device/technique.

The devices described herein are preferably portable, inexpensive and easy to use. It is envisioned that the devices would be available to individuals as well as professionals. Professionals could use the instant invention as quick diagnostic tools for detecting bone integrity, e.g., fractures, bone density, etc., in an ordinary examine room without the need for sending the patient to a separate room or facility (as with certain existing technology). The objective for individuals could be monitoring bone quality at home, thereby avoiding expensive doctor visits.

Figure 3:
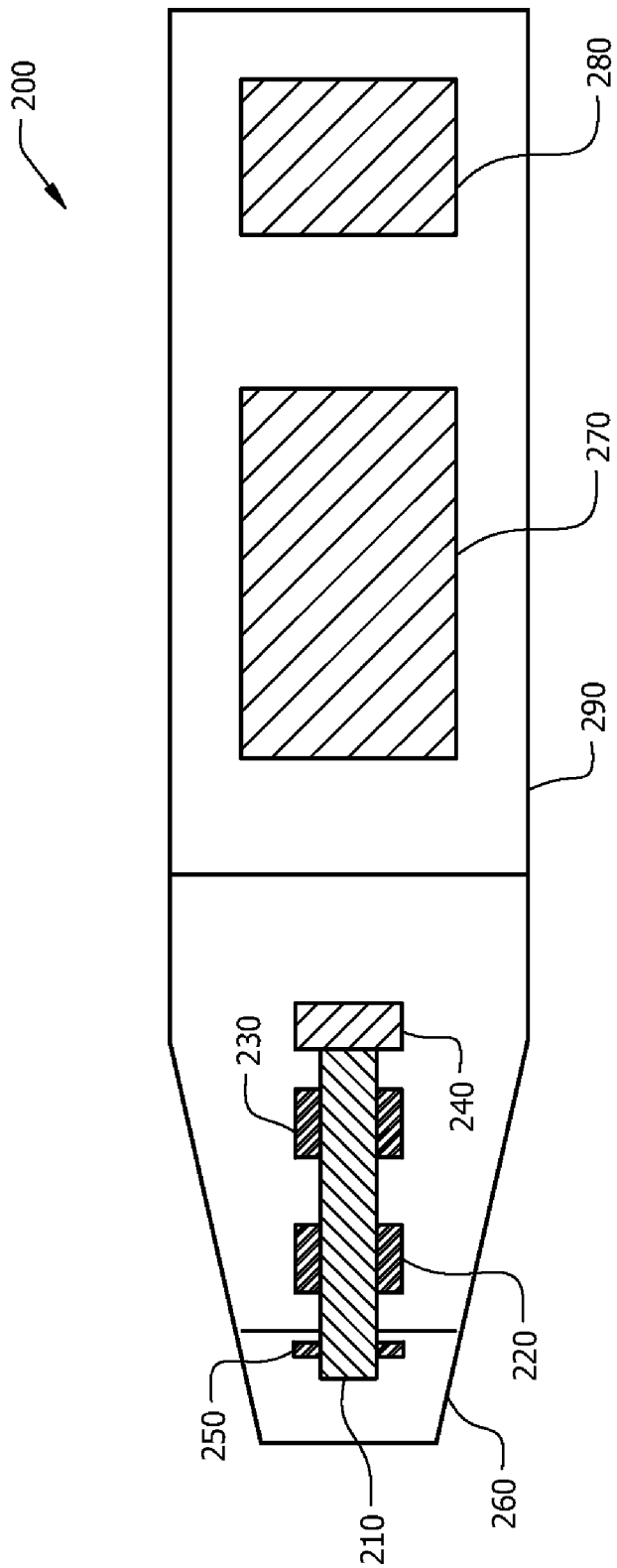
FIG. 3 shows another embodiment of a portable tissue characterization device in accordance with one or more principles of the present invention.

FIG. 3 shows another embodiment comprising of a portable device 200 comprising a piston 210, an acceleration means 220, an electromagnet 230, an optional accelerometer 240, a load cell 250, a contact tip 260, circuitry 270, an energy source 280 and an external housing 290. The operating piston 210 could be made of any suitable material such as plastic or metal, preferably metal. The basic components are known in the art and readily understood by those of ordinary skill. The contact tip 260 may be made of any suitable material such as plastic or metal, preferably plastic. The contact tip 260 and piston 210 may be integrally connected such that the movement of the piston 210 necessarily moves the contact tip 260. Alternatively, the piston 210 may not be integrally connected to the contact tip 260. In other words, piston 210 would move independent of contact tip 260 through a through bore in the contact tip 260 such that piston 210 could directly contact the designated area being tested.

In either embodiment, the contact tip 260 is in communication with load cell 250 so that a predetermined amount of contact force may be applied to a designated area for testing. Load cell 250 may be used to determine if an appropriate amount of force is being applied to the target area prior to initiating the test procedure. If piston 210 and contact tip 260 are connected, then piston 210 must overcome the force being applied to the target area via the contact tip 260 for operation and data collection. If piston 210 moves independent of contact tip 260 then piston 210 would not have to overcome the pre-applied force at the target area. One skilled in the art will appreciate that such a design alternative may be a consideration in selecting the appropriate mechanism for moving piston 210 during operation. The acceleration means 220 should be able to accelerate piston 210 over a frequency range of about 20 Hz to about 600 KHz.

Circuitry 270 may comprise a processor and data storage means (not shown). The processor, preferably a microprocessor, may comprise any known in the art and should be capable of performing the functions described herein. The data storage means may comprise any means capable of storing data collected during operation including the parameters of the testing device for a given data sample collected. Also the circuitry must be capable of allowing the stored data to be transferred to a remote device, preferably a stand alone computer or similar device. Accordingly, portable device 200 may comprise a means (wireless or otherwise) for transferring data (either live or stored) to a remote device such as a computer. Suitable non-wireless alternatives may comprise, but are not limited to, direct wiring to the remote device, ports that allow for connective wiring to the remote device and/or ports that allow communication through a cradle device (wherein the cradle device is in communication with the remote device.

Circuitry 270 may also comprise external components such as a display means and one or more input means. For example, one embodiment may comprise one or more of the following: (a) an external toggle switch or button for powering on and off the device, (b) one or more entry buttons for selecting operating parameters, e.g., anatomic area (arm, hip, spine, etc) to be tested, male vs female, age, etc., (c) one or more LED's , lights, speakers or other audio device to indicate readiness, that the preload has been achieved, confirmation/rejection of data collection, battery status, etc., and/or (d) a display panel, audio means or other means for displaying or indicating a message, such as a number or text message.

Energy source 280 may comprise a portable energy device, such as one or more batteries, or a means for transferring electricity to the circuitry 270, such as electrical connections and necessary devices for making a standard connection with an electrical outlet. For embodiments using portable energy, the energy source 280 may include a receptacle for receiving the one or more batteries and optionally a means for recharging said batteries if applicable. All such simple electrical circuitry is readily known in the art.

Figure 4:
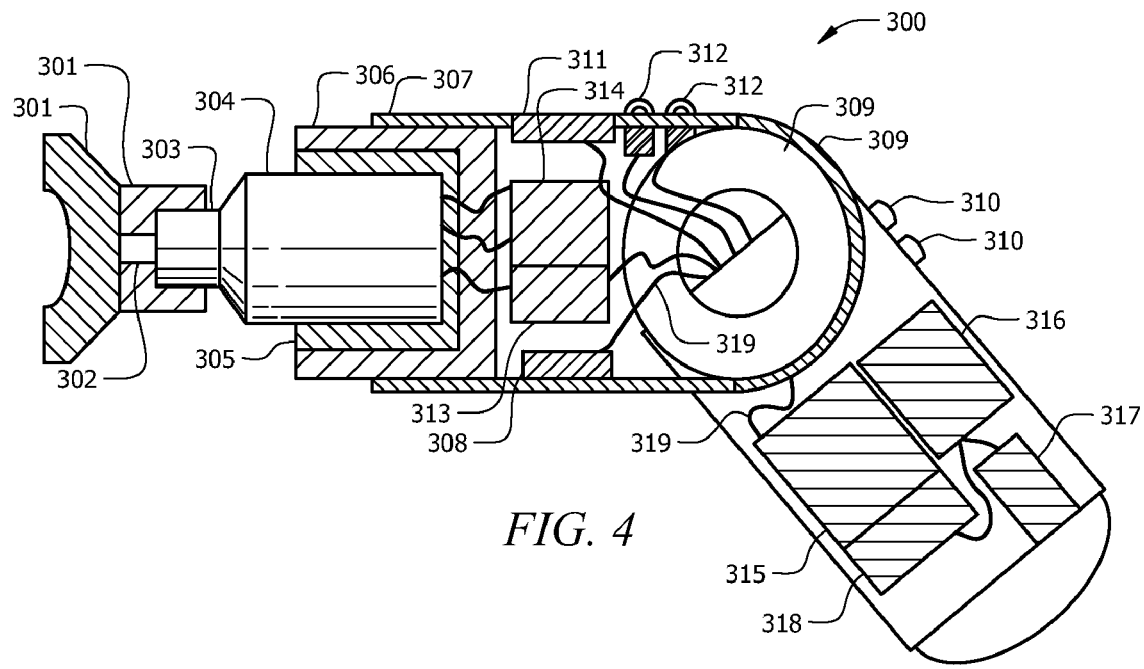
FIG. 4 shows another embodiment of a portable tissue characterization device in accordance with one or more principles of the present invention.

FIG. 4 shows another embodiment comprising a device 300 including contact tip 301, piston 302, impedance head 303, vibration generator 304, vibration insulator 305, vibration generator housing 306, outer housing 307, preload cell 308, hinge 309 (optional), manual inputs 310, display 311, indicator outputs 312, power amplifier 313, charge amplifier for the receiving signal 314, circuitry 315, power pack (energy source) 316, data transmitter 317, data storage 318 and various electrical connectors 319 as needed.

All housing and/or non-electrical type components, e.g., Contact tip 301, piston 302, vibration generator housing 306, outer housing 307, hinge 309, etc., may comprise any suitable material such as plastic or metal, preferably plastic. Contact tip 301 may comprise any shape, e.g., flat or concave, and may be easily exchangeable with various shaped tips designed for particular anatomical regions. Piston 302 is preferably a threaded rod.

Impedance head 303 preferably comprises a means for measuring both the vibration (frequency sweep) produced by device 300 to excite the tissue being tested and the tissue response to the excitation. Vibration generator 304 preferably comprises a shaker, wherein the shaker induces vibration in the tissue or excites the tissue being tested using one or more devices selected from the group consisting of a piezoelectrical device, an electromagnetic device, an electromechanical device, a pneumatic device and a hydraulic device. Vibration insulator 305 and vibration generator housing 306 may alternatively comprise a single entity that is able to perform both functions. Vibration insulator 305 dampens the generated vibration or frequency sweep to improve the integrity of the signal and prevent transfer to the outer housing 307 and user hand. Preload cell 308 measures the deformation of the outer housing 307, thereby indicating contact force between device and testing object.

Manual inputs 310 may comprise one or more buttons or keypads for powering device 300 and/or selecting operational parameters. Typical operational parameters may include anatomical site to be tested, age of patient, sex of patient, body weight, shoe size, file name for test data, and the like. Display 311 may comprise any display means known in the art and is not critical to the invention. For example, display 311 may comprise an LCD screen. Likewise, indicator outputs 312 may comprise any technology known in the art such as LED technology. Indicator outputs 312 may flash or otherwise indicate when the appropriate load is being applied for a test run, when a valid set of data has been collected, and the like. Inputs 310, display 311 and outputs 312 may alternatively be combined as technology allows and comprise one or more of the following: (a) an external toggle switch or button for powering on and off the device, (b) one or more entry buttons for selecting operating parameters, e.g., anatomic area (arm, hip, spine, etc) to be tested, sex of patient, age, etc., (c) one or more LED's, lights, speakers or other audio device to indicate readiness, that the preload has been achieved, confirmation/rejection of data collection, battery status, etc., and/or (d) a display panel, audio means or other means for displaying or indicating a message, such as a number, text or graphic type message.

Power amplifier 313 increases the signal from the signal generator (not shown) contained in circuitry 315 and drives the vibration generator 304. Charge amplifier 314 converts the charge output from a piezoelectric, capacitive or other charge-producing sensor to a signal such as analog voltage or current.

As with all embodiments, circuitry 315 may comprise a processor and data storage means. As shown, data storage means may comprise a separate storage device 318. The processor, preferably a microprocessor, may comprise any known in the art and should be capable of performing the functions described herein. The data storage means (whether part of circuitry 315 or as a separate component 318 may comprise any means capable of storing data collected during operation including the parameters of the testing device for a given data sample collected. Also the circuitry must be capable of allowing the stored data to be transferred to a remote device, preferably a stand alone computer or similar device. Accordingly, circuitry 315 or component 317 may comprise a transmitter (wireless or otherwise) for transferring data (either live or stored) to a remote device such as a computer. Suitable non-wireless alternatives may comprise, but are not limited to, direct wiring to the remote device, ports that allow for connective wiring to the remote device and/or ports that allow communication through a cradle device (wherein a cradle device is in communication with the remote device.

As stated previously, power pack 316 may comprise a portable energy component, such as one or more batteries, or a means for transferring electricity to the circuitry 315, such as electrical connections and/or necessary devices for making a standard connection with an electrical outlet e.g., cables or cords. For embodiments using portable energy, the energy source 316 may include a receptacle for receiving the one or more batteries and optionally a means for recharging said batteries if applicable. All such simple electrical circuitry is readily known in the art.

Figure 5:
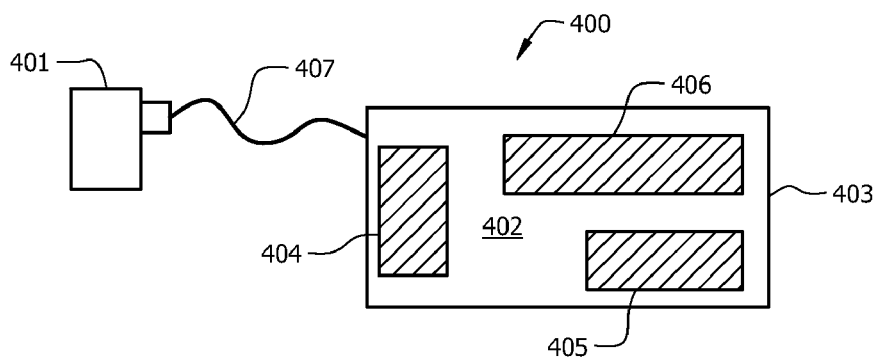
FIG. 5 shows one embodiment of a portable extension device in accordance with one or more principles of the present invention.

FIG. 5 shows a portable extension 400 comprising a sensor 401 and circuitry 402 connected by wire 407. For all embodiments of the present invention, wireless connections (where technologically available) are interchangeable for hardwired connections. Circuitry 402 comprises a housing or platform 403, processor 404 and transmitter 405. Transmitter 405 may be integrated as part of processor 404 (not shown). Alternatively, sensor 401 and circuitry 402 may be integrated into a single structure. Other embodiments of the present invention comprise multiple sensors each with its own corresponding circuitry or, alternatively, multiple sensors connected to a single portable circuitry. Regardless, the processor 404, transmitter 405 and energy source 406 comprise similar components as described in connection with other embodiments described herein. The data collected by the portable extension should be capable of transmitting via transmitter 405 or processor 404 said data from the portable extension 400 to either the primary device (such as device 300 described in FIG. 4) or to a remote device such as a computer.

Figure 6:
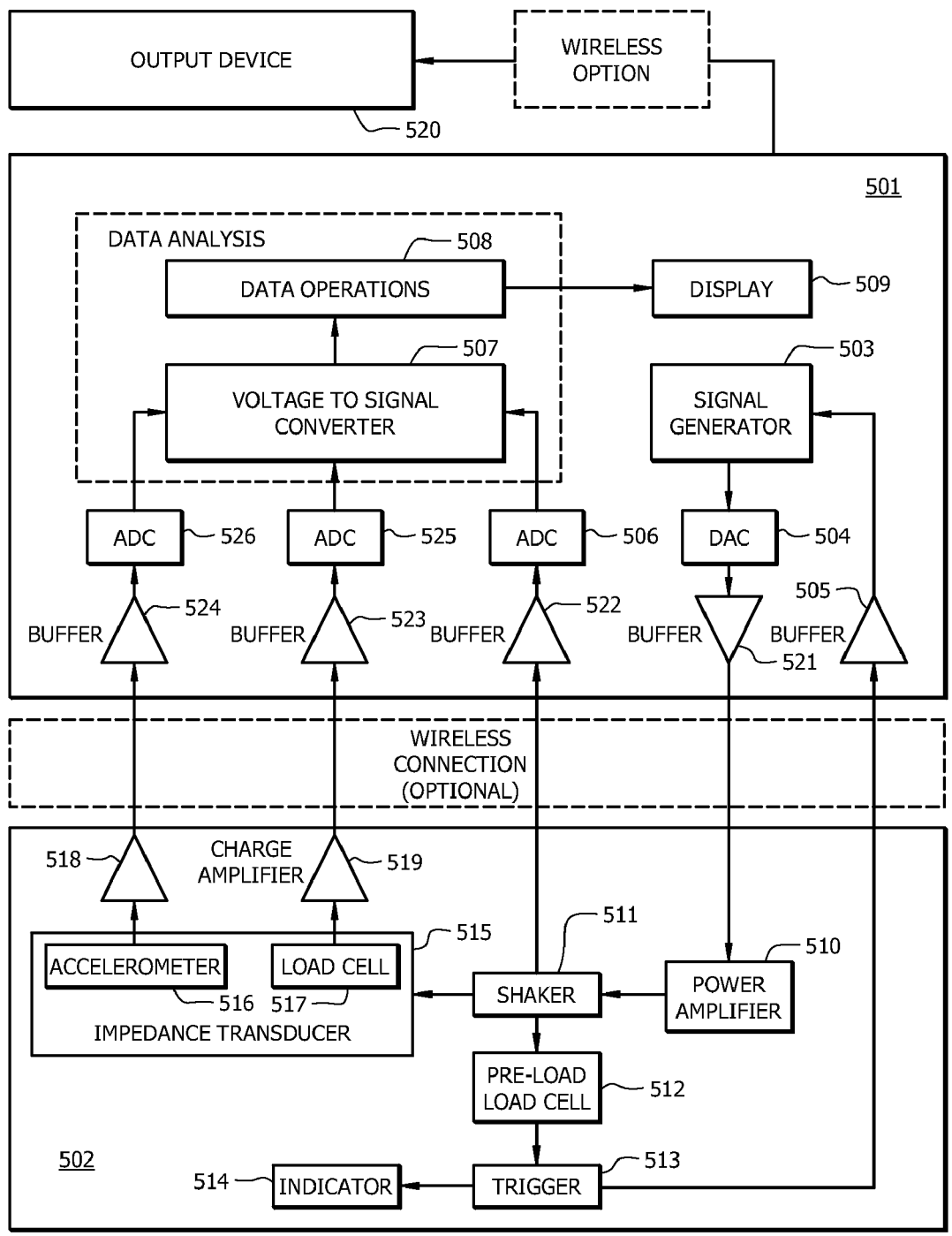
FIG. 6 shows a schematic illustration of one embodiment of a portable tissue characterization device in accordance with the principles of the present invention.

FIG. 6 shows a schematic of one embodiment for a portable device 500 in accordance with of the general principles of the present invention. It is worth noting that the invention is not limited to the exact representation in FIG. 6, but instead FIG. 6 is provided to give greater clarity by way of a specific example. One of ordinary skill will understand that many modifications to such an exact schematic are possible without leaving the spirit and scope of the invention. For example, charge amplifiers and/or buffers are easily moved within the device from one unit to another or combined to a single circuitry.

Accordingly, portable device 500 comprises a processor unit 501 and mechanical unit 502. Processor unit 501 comprises signal generator 503, digital to analog converter 504, a plurality of buffers 505, 521, 522, 523, 524, a plurality of analog to digital converters 506, 525, 526, voltage to signal converter 507, a processor 508, and display 509. Mechanical unit 502 comprises power amplifier 510, shaker 511, preload load cell 512, trigger 513, indicator 514, and impedance transducer 515. Impedance transducer 515 comprises accelerometer 516 and load cell 517. Mechanical unit 502 may also comprise charge amplifiers 518, 519 to correspond to accelerometer 516 and load cell 517, respectively. Optionally, device 500 comprises one or more stand alone output device 520 such as a monitor, LCD screen, plotter, printer, storage unit, and the like. Processor unit 501 communicates with mechanical unit 502 and output device(s) 520 using either hardwired or wireless connections.

Another embodiment of the present invention comprises a method for collecting data regarding tissue characteristics using one or more of the device embodiments or obvious variations thereof described herein. Collecting the data sample may be accomplished by applying a load to the target area, i.e., pressing the contact tip of the device to the skin, bone, or implant until an indicator on the device displays that sufficient force has been applied. Once the load is applied, the shaker would be activated, either manually or automatically, to cause the piston to accelerate at a frequency range of about 20 Hz to about 600 KHz. An accelerometer and/or other device may then measure the resulting force and/or acceleration of the piston and the data would be stored in the circuitry storage means.

Once data has been collected, an output signal can confirm the sample collected appears useable and a new sample can be collected. One or more samples may be collected and 3 or more are preferable. The collected data samples can then be evaluated. Evaluation may take place within the device itself depending upon the sophistication of the software/hardware. Alternatively, the device may transfer the data to a computer or other device for evaluation.

The data may be evaluated against previous measurements taken by the patient or with a database of known measurements. In general, the data should be manipulated using an algorithm to analyze the data and produce a value. It is preferred that evaluation be carried out by using the calculated value and comparing it with other values calculated in a similar manner. Once evaluated an output may be generated such as a simple yes/no, a percentage value of bone integrity, an extrapolated value for bone integrity and/or a normalized value having significance with the patient.

In one embodiment, the database values would be stored in the remote computer. Periodic updates may be downloaded to enlarge the number of values available for comparison. Alternatively, the database values may be stored on a second remote device accessible via the internet, such that evaluation may comprise sending the collected data and/or calculated values via the internet to the second remote device for evaluation and/or comparison. In these embodiments, the second remote device would reply with the output signal described above.

FIG. 6 schematic may also be used to illustrate, in general, one embodiment for a testing method of the present invention. A load is placed on an anatomic region of a patient, preferably a location that has a thin layer of soft tissue over a bone. The preload load cell 512 measures the load and activates a trigger 513 that in turn can activate an indicator 514 so that the user may identify when the appropriate load is achieved for testing. The load range should be in the range of about 10 Newtons (N) to about 100 N, preferably from about 10 N to about 20 N. Alternatively, trigger 513 may automatically activate the testing sequence by activating signal generator 503 and optionally initialize software.

Signal generator 503 produces a signal capable of activating shaker 511. As shown, the signal is a digital voltage signal that is converted via the digital to analog converter 504. After passing through buffer 521, the signal is amplified (if necessary) via power amplifier 510, which in turn powers shaker 511. Shaker 511 generates a vibration or frequency sweep that can be transmitted into the tissue at the point under load via a contact tip 301 in connection with shaker 511, preferably by means of a rod and casing (not shown). The contact tip is also operative connected to an impedance transducer 515 having components 517, 516 for measuring the signal going out (i.e., signal being transferred into the tissue) and the responsive signal, respectively. As shown, component 515 comprises an accelerometer 516 and comprises a load cell 517.

The signal generator 503, power amplifier 510 and shaker 511 produce a vibration or frequency sweep over a specified range based on a given set of operational parameters such as anatomic site, age and sex of the patient. One or more of these operational parameters may be inputted by the user prior to, during or after the preload load is executed, preferably prior to placing the region under load. Low and high frequencies are utilized. A preferred frequency sweep range is from about 20 Hz to about 1.5 MHz. The preferred low frequency is from about 20 Hz to about 600 kHz and high frequency is from about 800 Hz to about 1.5 MHz.

The input and output signals are measured via load cell 517 and accelerometer 516, respectively, and transmitted to the voltage to signal converter 507. The signals may be amplified using charge amplifiers 518 (responsive signal), 519 (outgoing signal), optionally buffered via buffers 524, 523 and converted in analog to digital converters 526 (responsive signal), 525 (outgoing signal) prior to reaching the voltage to signal converter 507. The converted signal may then be processed by processor 508 to produce a user response.

A user response may be communicated via an output device, such as a display panel, audio means or other means for displaying or indicating a message, such as a number, text or graphic type message. Any output device known in the art is sufficient. In one embodiment, generating a user response may comprise processor 508 calculating a relative value based on comparative data from a database. Alternatively, generating a user response may comprise processor 508 calculating a relative value based on an analytical method. In yet another embodiment, the user response may comprise a diagnostic value for osteoporosis or bone fractures.

Other embodiments may include one or more of the basic steps of (a) selecting an anatomical region for testing; (b) selecting operational parameters; (c) apply a force to the anatomical region to achieve constant contact pressure with the region; (d) inducing a frequency sweep at the anatomical region while maintaining contact pressure; (e) collecting tissue response data; and (f) providing a response based on the data from step (e). Step (f) may comprise one or more of the following steps (i) confirming that the data collected in step (e) was a valid sample; (ii) calculating one or more raw values based on the data collected in step (e); (iii) comparing the raw values from (ii) to either: (1) one or more previous calculated raw values for a given patient at the same anatomic site, (2) one or more previous calculated raw values for a given patient of his/her contralateral side (if available), or (3) a database of similar values; (iv) determining a relative diagnosis based on the comparison in step (iii); and (v) communicating the relative diagnosis to a user. Further, the response of step (f) may comprise one or more forms selected from the group consisting of alpha-numeric characters, electronic data, graphs, pictures, video, charts, icons or sounds.

Figure 7:
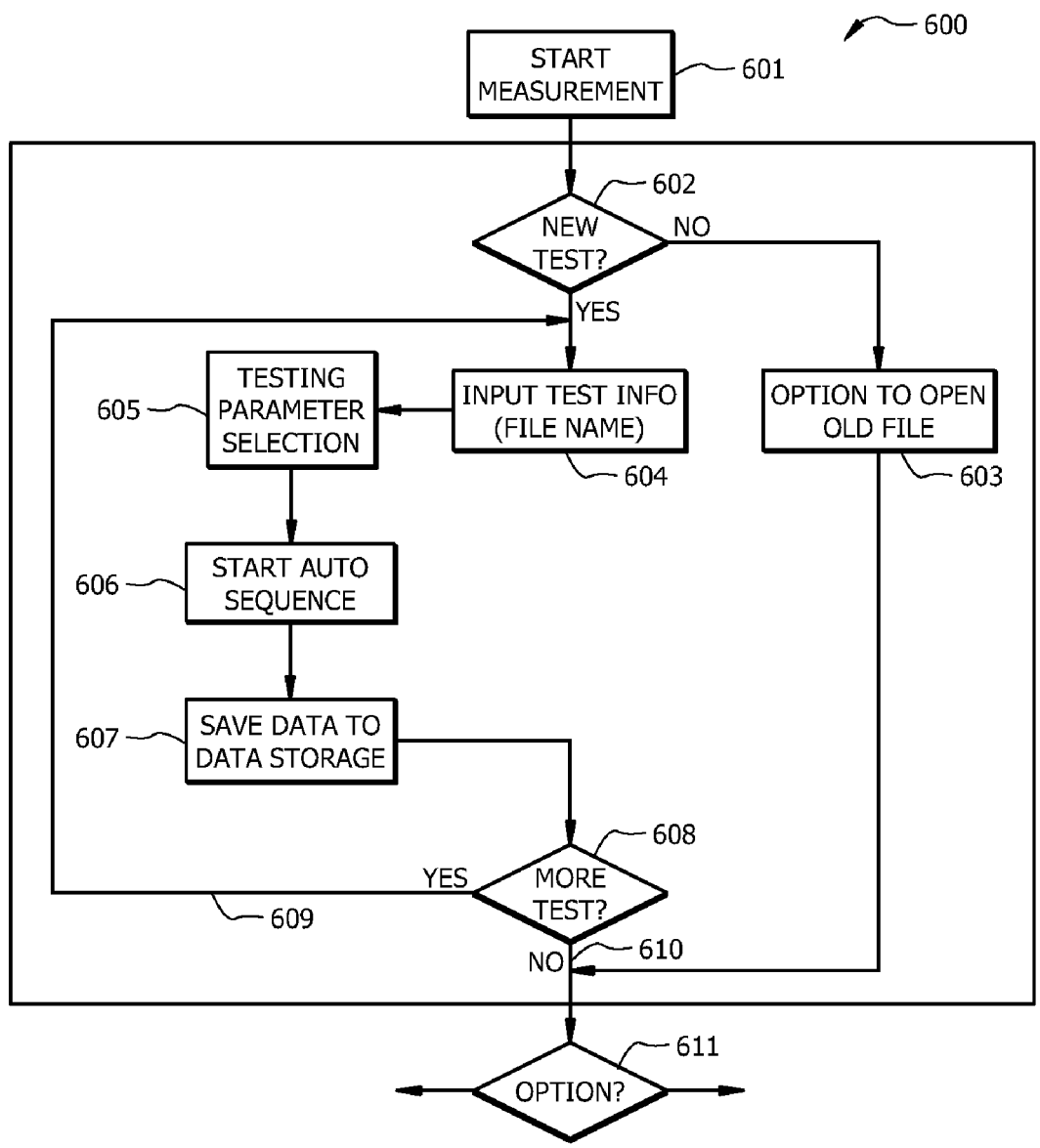
FIG. 7 shows one embodiment for data collection in accordance with one or more principles of the present invention.

FIG. 7 shows a flow chart 600 illustrating a method for data collection in accordance with one embodiment of the present invention. The user or some other trigger initiates 601 the start measurement sequence. The user is allowed to choose a new test sequence or open an existing set of data 602. If the user does not choose a new test, she/he can select from one or more old data sets and optionally other choices 603. Opening an old set of data prompts additional options to manipulate, transfer, save or otherwise use the data 611. If the new test option is selected at 602 then the user is prompted to input a file name 604. The user can then select operational parameters 605 as have been described herein. The testing or data generation is then conducted by initiating an auto sequence program 606. Once collected the data is saved to temporary or permanent storage 607 and the user is prompted to select whether or not more tests are to be run 608. If more tests are selected the user is then taken back 609 to action 604 and the sequence repeats. If no additional tests are selected the user is prompted for additional options to manipulate, transfer, save or otherwise use the data collected.

Figure 8:
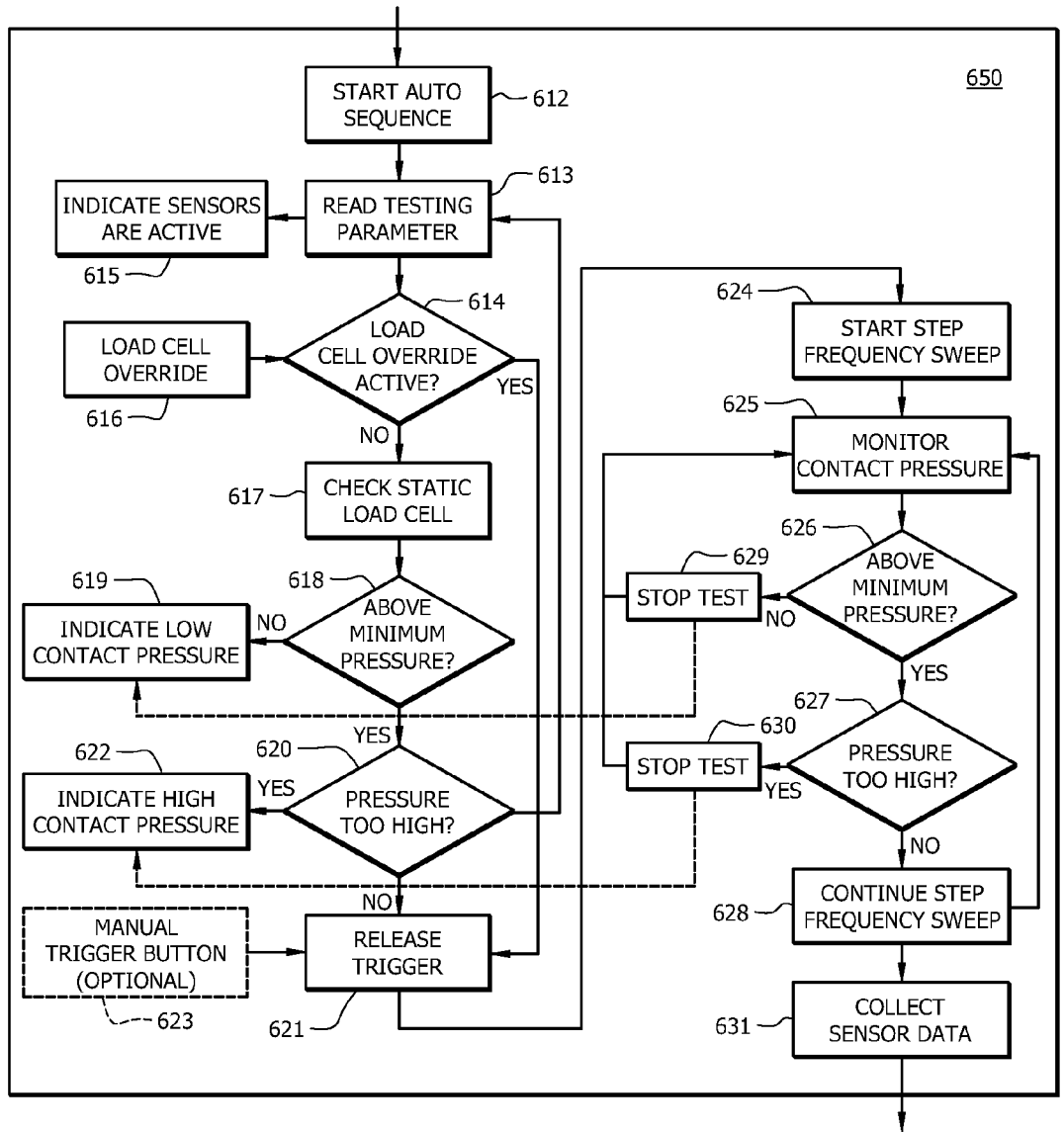
FIG. 8 shows one embodiment for a testing sequence in accordance with one or more principles of the present invention.

FIG. 8 shows a flow chart 650 illustrating a method for the testing sequence in accordance with one embodiment the present invention. Once the auto sequence program is initiated 612 a processor reads the operating parameters 613 (comprising at least one or more user inputs). The system is checked and indicates active sensors 615. At this point the user should be applying a force against the tissue by pressing the tip against the anatomic region to be tested. A load cell override 616 may be selected 614. If selected the testing sequence will be triggered 621. Alternatively, the user may depress a manual trigger 623, which would trigger the testing sequence 621. If no load cell override command is activated, then the static force measured within the housing will be evaluated 617 to determine if the force is too low 618 or too high 620 and result in a too low 619 or too high 622 contact force alert. Static force that maintains within a specified range will allow the release trigger to start the testing sequence 621.

Once initiated, a frequency sweep will start 624 over a specified range. Contact force is monitored 625 throughout the frequency sweep duration. If the contact force falls below the minimum 626 the sweep is terminated 629 and a low-force indicator is activated 619. If the contact force becomes too great 627 the sweep is terminated 630 and a high-force-indicator is activated 622. A frequency sweep that is achieved without a contact force violation continues over the entire specified range 628. The responsive signal from the tissue is collected as sensor data 631.

Figure 9:
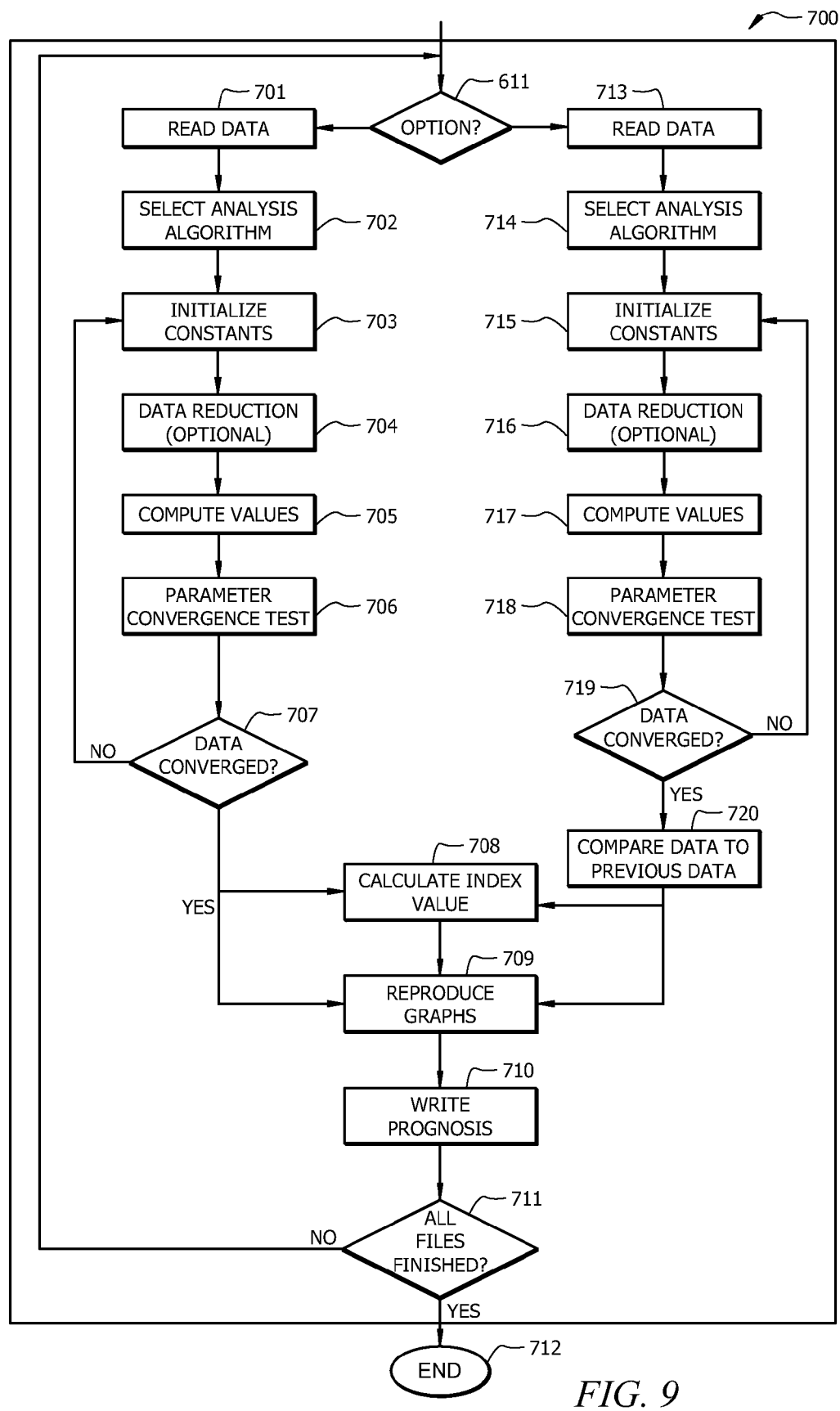
FIG. 9 shows one embodiment for data analysis in accordance with one or more principles of the present invention.

FIG. 9 shows a flow chart 700 illustrating a method for data analysis in accordance with one embodiment of the present invention. The user may select from options 611. Option may comprise, among other things, obtaining a raw response value or a comparative value. Obtaining a raw response value comprises the following steps: (1) data is loaded/read into a processor 701; (2) the user selects an analysis algorithm 702 (alternatively, this step may be omitted if an algorithm has been pre-selected); (3) constants are initialized 703; (4) an optional data reduction or filter process is carried out 704; (5) a value is calculated according to an analytical method 705; (6) a parameter convergence test is carried out 706 to determine if the value(s) are in an expected range 707 (if out of range the sequence is restarted at step (3)); converged data is used to either (a) calculate a user response value 708, or (b) produce a graphic response 709; (7) optionally create a prognosis based on comparing (6)(a) or (6)(b) with data from a database or look-up table; (8) prompt the user to select another analysis 611 or to end the analysis sequence 711. Selecting to end the analysis sequence at 711 will end the analysis sequence 712.

Obtaining a comparative value comprises the following steps: (1) data is loaded/read into a processor 713; (2) the user selects an analysis algorithm 714 (alternatively, this step may be omitted if an algorithm has been pre-selected); (3) constants are initialized 715; (4) an optional data reduction or filter process is carried out 716; (5) a value is calculated according to an analytical method 717; (6) a parameter convergence test is carried out 718 to determine if the value(s) are in an expected range 719 (if out of range the sequence is restarted at step (3)); converged data is compared with to a previous data set from the same patient to calculate (a) a comparative response value at 708, or (b) produce a graphic response 709; (7) optionally create a prognosis based on comparing (6)(a) or (6)(b) with data from a database or look-up table; (8) prompt the user to select another analysis 611 or to end the analysis sequence 711. Selecting to end the analysis sequence at 711 will end the analysis sequence 712. Differences measured between various data sets obtained (i.e., transfer function results obtained at different time points) for the same subject are indicative of changes within the soft and/or hard tissue. In a similar manner, comparison to a standard database can be made, or on the contralateral side if applicable.

Certain embodiments comprise the use of an analytical method. The following are basic analytical methods that are within the spirit and scope of one or more embodiments of the present invention. The methods are not intended to be limiting, but are provided by way of example for clarity.

Method 1.

Suitable analytical methods comprise calculating a ratio between a high frequency response of the tissue being tested and a low frequency response. Based on preliminary numerical analysis, the high frequency response can be used to determine the amount of trabeculae (bone tissue) present, while the low frequency response indicates the amount of those trabeculae being utilized for load transfer. A fraction close to one indicates healthy bone, whereas a fraction close to 0.5 is indicative of a very fragile bone. The low frequency response is measured at the first natural frequency mode, while the high frequency is in the upper kilohertz range.

It has been known that the inefficiency of load transmission is the principle cause for reduction of fracture load. This inefficiency is dependent on tissue level damage, which can be estimated by the fraction of struts belonging to a term called stress backbone. The required fraction can be obtained if the number of trabeculae (struts) that belong to the stress backbone and the total number of trabeculae on a sample of bone are known. The following observations provide a method to estimate these last two quantities. First, the elastic modulus $E(0)$ of a sample depends on the number of stress pathways. Each pathway allows additional load to be transmitted, and hence increases $E(0)$. Second, the response $E(\Omega)$ of the sample to (sonic or ultrasonic) vibrations of a sufficient high frequency $\Omega$ can be used to estimate the number of struts on the network. Under these conditions, signals are attenuated very quickly inside the sample, and stresses are limited to the immediate neighborhood of the surface that is driven. As a result, the presence of large fractures in the interior of the network, which reduce the extend of the stress backbone, play no role in the response to high-frequency driving; i.e., all available trabecular elements near the surface contribute to $E(\Omega)$. Hence, assuming that the trabecular perforation is (fairly) uniform within each layer of trabecular elements, $E(\Omega)$ can be used to estimate the total number of trabecular elements in the sample.

Thus, the ratio $\Gamma \equiv E(0)/E(\Omega)$, which can be obtained from vibrational analysis, provides an estimate of the fraction of struts belonging to the stress backbone. If, as we assume, the reduction in fracture load is related to the extend of the stress backbone, then the former is related to $\Gamma$.

Stated differently, this analytical method comprises calculating a ratio of low frequency response over high frequency response of a tissue sample. The low frequencies excite the trabeculae or struts throughout the entire bone length, i.e., low frequencies are able to penetrate the whole tissue being tested. This identifies the integrity of the sample or more correctly the amount of tissue that is still functioning properly, i.e., the mass of tissue that can still bear a load. The high frequencies do not excite or penetrate the entire tissue being tested. Instead, higher frequencies penetrate only a thin layer of the tissue, but identify a total mass across in that plane. The total mass can then be projected out for the tissue being tested. It is assumed that a nearly uniform mass distribution exists in the tissue. Accordingly, the ratio of low frequency over high frequency responses gives a percentage of the amount of active "load bearing" tissue.

Method 2.

Another embodiment comprises using an analytical method comprising a step-wise frequency sweep being applied to the object being tested. The frequency sweep starts at a low frequency, preferably 20 Hz, and stops at a high frequency, generally about 2000 Hz (preferably 100-1000 Hz, with a predetermined step function. The data recorded from an accelerometer, load cell, and driving signal in the time domain are converted to a frequency domain using a discrete Fourier Transformation at each driving frequency. Various filters (known and understood by one of ordinary skill in the art) are used for data smoothing and reduction of noise.

The data are normalized to the maximum peak measured at any frequency. A two-dimensional plot is generated with one axis being the driving frequency (step-wise frequency), and the other axis the frequency spectrum as analyzed using the Fourier Transformation. The amplitude may be color coded to visualize variations in signal intensity. A log or linear color scheme can be used, preferably log scale. A pattern analysis approach is used to identify regions that change according to the pathology, for example osteoporosis. Different regions of the plot represent responses of various tissues. The low frequency response represents the interaction between soft and hard tissue, an intermediate region includes the resonance of bone and information of its mass, while the high frequency region contains information about the soft tissue properties. Therefore, variations in patterns obtained from the aforementioned 2D plot can provide information on bone quality, apparent damage, and joint properties. In addition, a database of plots from known tissue samples (patients with known problems) can provide comparative results. Further, it is believed that the plots may also be used to separate joint problems (i.e., herniated disc or facet joint pathologies) from bone tissue problems.

Method 3.

In an alternative approach, the Fourier transformed signals described in the methods above may be used to calculate other mechanical transfer functions such as accelerance, effective mass, mobility, impedance, compliance, and stiffness in addition to cumulative energy. Table 1 below lists the various functions that may be calculated from the data and Fourier transformed signals generated in accordance with the various embodiments of the present invention. A similar pattern recognition method as identified above is utilized to identify changes between measurements and to provide an indication for the progression of the pathology or healing/treatment.

| Mechanical Vibration Transfer Functions | Definition |
| --- | --- |
| Accelerance | Acceleration/Force |
| Effective Mass | Force/Acceleration |
| Mobility | Velocity/Force |
| Impedance | Force/Velocity |
| Compliance | Deformation/Force |
| Stiffness | Force/Deformation |

Method 4.

An alternative approach to Method 2 is to utilize Fast Fourier Analysis of the recorded signal for a particular excitation frequency range, preferably at a width of 200 Hz. Multiple analysis at various frequency intervals may be conducted. For each frequency range, one or more of accelerance, effective mass, mobility, impedance, compliance, stiffness, and cumulative energy may be determined, as they represent mechanical vibration transfer functions derived from various excitation (input) and response (output) signals. Variations in these signals/spectra for the different frequency ranges are indicative of damage to the different tissue types, such as hard or soft tissue.

Method 5.

A variation of Method 4 comprises analyzing only single frequency steps. A discrete Fourier Transformation can be utilized to convert the time dependent signal into a frequency domain. Mechanical transfer functions and cumulative energy may be calculated. Peaks of the different modes of the mechanical transfer functions can be plotted cumulatively in one or more graphs. Shape changes, ratios between first and consecutive peaks, slopes, and more may be calculated from the graph. Variations in these signals/spectra for the different input frequencies selected are indicative of damage to the different tissue types, such as hard or soft tissue.

Method 6.

A log or linear frequency sweep is used to test a patient's bone. After Fast Fourier Analysis of the output signal (accelerometer) a spectral analysis is performed on the low frequency range to determine bone mass. Based on known anthropometric data, bone size can be estimated from the calculated bone mass. The natural frequency is determined from the peak analysis of the frequency spectra. A well established correlation between bone size times natural frequency and age is used to calculate a parameter that can separate normal aging patients with patients suffering from excessive bone loss or bone micro-damage. Alternatively, the value for bone mass is multiplied with the natural frequency directly and used as a predictor of pathology.

Method 7.

This technique differs from previous techniques in that it uses much more information from the vibrational behavior of tissue. The models include mass elements, springs, and dashpots, representing the various tissues and joints. A simplified viscoelastic model will be used to fit the experimental data after curve fitting and regression analysis. This model may contain only three elements (mass, spring, dashpot) to describe a differential equation for acceleration, velocity and displacement behavior over various frequencies. Utilizing a least-square method, parameter fitting will be conducted to estimate values for the three elements (mass, spring, dashpot). The viscoelastic parameters obtained, will be used as initial guess values for a more complex viscoelastic model, which will include the flesh, bone, and the joints. A similar least-square method will be utilized to obtain values for the differential equation representing the more complex viscoelastic model. The viscoelastic model will assist in separating the dynamic response measured with the accelerometer and load cell for the different tissue components. The parameter values are directly related to biomechanical properties of the tissue. Pathological disease and sources for pain can easily be identified using this approach.

Method 8.

In predicting fracture risk, one has to know the strength of a material and the load it is subjected to during regular activities. The following technique calculates the ratio of predicted bone strength and normal postural load experienced by human vertebral bodies within an anatomic region. Subjects are tested in an unloaded state and subsequently in a loaded state; for the spine, this would correspond to a laid down position and standing up, respectively. Based on the vibration response of the tissue and the data obtained through this methodology an estimate of the physical load applied to the bone tissue in vivo is feasible. In applying principles mentioned in method 7, material properties such as stiffness of the bone tissue can be determined for the un-loaded and loaded case. The difference in vibrational reading between the two cases is to the largest extent due to the loading of the tissue in moving from the laid down position to an upright position. This difference can be expressed as deformation of the tissue due to loading, which in turn is a measure of stiffness. Using the stiffness-strength correlation, a fracture risk prediction can be performed. Again, a viscoelastic model may be used to fit the recorded data and deliver the physical quantities to describe the loading and tissue behavior. Currently, there is no known method to assess loading conditions in vivo. Published data are back calculations based on body mass distribution or inverse kinematics analysis. A similar procedure may be developed for the femoral neck.

Another embodiment of the present invention comprises using the apparatus described herein as a therapeutic tool, particularly in the area of chiropractics, pain relief, bone growth stimulation, bone healing (particularly after surgery) and osteoporosis treatment at selected anatomic sites. Such embodiments generally comprise finding the natural frequency for a specified tissue in order to induce the maximum excitation of the tissue. Based on current knowledge known to the field, the human body's capability to regenerate tissue is based on dynamic mechanical loading, this is particularly the case of hard tissue like bone and cartilage. Cartilage is an avascular tissue, which though compression and relaxation transports nutrition and removes waste products. In bone, sportive activities such as bicycling or swimming have shown to effect bone tissue to a minor extent, while high impact high frequency loading such as jogging can stabilize or even increase bone mass. The exact mechanism behind the dynamic loading response is not known yet The objective of our device is to regionally stimulate tissue though vibration, thereby promoting and increasing the regenerative and healing response. In applying a vibrational stimulus to tissue at the resonance frequency, the maximal amount of energy is transmitted to the tissue.

One embodiment of the invention comprises a business method wherein the techniques described above are carried out and a fee is charged either for the updates to additional data and/or for access to the second remote computer having a dynamic database via the internet. The fee may include (1) a one-time fee, (2) an upfront or reoccurring multiple access fee, (3) a lifetime access fee, or (4) some combination thereof. Another embodiment includes a method for building a database via the internet.

For example, a user may utilize a portable tissue characterization device in accordance with one or more of the embodiments described herein to obtain individual testing data for one or more specific anatomic regions. The user may then transmit via the internet that data to a remote device (such as a computer) via a hardwired or wireless connection. Alternatively, the device may dock in a cradle that can facilitate the transmission of the data to the remote device. The remote device may perform a data analysis (1) based on one or more analytical methods as described herein, (2) based on comparative data (from the earlier testing by the same patient) stored on the remote device, and/or (3) based on comparative data from a look-up table downloaded from a central server or generated in house from multiple patients. A response value can then be generated and communicated to the user or other party based on the data analysis.

Alternatively, the user transmits testing data to a central server for data analysis. The central server receives the data and performs the data analysis (1) based on one or more analytical methods as described herein, (2) based on comparative data (from the earlier testing by the same patient) previously or contemporaneously transmitted to the central server, and/or (3) based on comparative data from a look-up table stored at the central server. A response value can then be generated and communicated to the user or other party based on the data analysis. This embodiment also describes a method for generating a database of patient testing data. As more subscribers/users send in patient information the database grows and provides more accurate response values. A patient's information may be stored indefinitely, such that the patient may at a subsequent date submit new testing data for comparison with his/her previous data and/or with the entire database Access is preferably based on a subscription fee. In order to receive a response value, new data (including biographical information about the corresponding patient) would need to be submitted in along with the access fee. It should be understood that prolific users, such as a doctor's office, may pay a one time fee or set fee for multiple analyses. Another embodiment allows the patient to access his/her data for monitoring, further analysis or review at anytime via the internet.

The patient may use the portable device in the privacy of his/her own home without the need for nurses, doctors or technicians. Thus, in an alternative embodiment, the patent's data may be transmitted either as described above directly to the central server from the patient's remote device to receive a response value or to a doctor who can monitor and forward the data to the central server for the response value. Alternatively, the patient may submit the data directly to the central server and the doctor may monitor by accessing the central server with the permission of the patient. This allows remote diagnosis, which may be more desirable for both the patient and doctor.

While preferred specific embodiments of this invention have been shown and described, modification thereof can be made by one skilled in the art without departing from the spirit or teaching of this invention. The embodiments described herein are exemplary only and are not limiting. Many variations and modifications of the apparatus and methods are possible and are within the scope of this invention. For example, while a piezoelectric element has been described as the actuator, a spring-loaded device, such as sold by Activator Methods Inc. for chiropractors, may alternatively be used as the actuator. Depending on in vivo measurements, another alternative, an acoustic actuator, may be used. Additionally, the data acquisition system may comprise a system built on a cart, which includes a computer, software, storage and networking capabilities. Alternatively, the data acquisition system may comprise a portable system connectable to a laptop computer for field usage and possible on-site data analysis. Thus, the scope of protection is not limited to the embodiments described herein, but is only limited by the claims, the scope of which shall include all equivalents of the subject matter of the claims.

What is claimed is:

1. A method for tissue quality assessment comprising:
    (a) engaging a tissue with a handheld device at a contact point and with a contact load, wherein the handheld device comprises a vibration generator for inducing mechanical vibrations over a range of frequencies at the contact point and one or more sensors for measuring the applied force of the mechanical vibrations and for measuring the tissue response at the same contact point;
    (b) initiating a frequency sweep at the same contact point in (a) with the handheld device;
    (c) simultaneously performing the frequency sweep over the range of frequencies based on a given set of operational parameters while maintaining the contact load to induce mechanical vibrations in the tissue at the same contact point in (a) and
    measuring the applied force of the mechanical vibrations and the tissue response at the same contact point in (a) with the handheld device to assess tissue quality.

2. The method according to claim 1 wherein the frequency range is between 20 Hz and 1.5 MHz.

3. The method according to claim 2 wherein the frequency range is between 20 Hz and 600 kHz.

4. The method according to claim 2 wherein the frequency range is between 800 Hz and 1.5 MHz.

5. The method according to claim 1 further comprising selecting the operational parameters prior to engaging the tissue with the handheld device.

6. The method according to claim 5 wherein the operational parameters comprise one or more inputs selected from the group consisting of anatomic site, age, sex, body weight and shoe size.

7. The method according to claim 1 wherein providing a user response comprises calculating a relative value based on comparative data from a database.

8. The method according to claim 7 wherein the user response comprises a diagnostic value for osteoporosis.

9. The method according to claim 1 wherein providing a user response comprises calculating a relative value based on an analytical method.

10. The method according to claim 1 wherein the user response comprises a diagnostic value for bone fractures.

11. The method according to claim 1 wherein the vibration generator comprises a shaker.

12. The method according to claim 11 wherein the shaker comprises a device selected from the group consisting of piezoelectric devices, electromechanical devices, hydraulic devices and pneumatic devices.

13. The method according to claim 11 wherein the shaker comprises an electromagnetic device.

14. The method according to claim 1 wherein one or more sensors comprises an impedance transducer.

15. The method according to claim 14 wherein the impedance transducer measures both input and output signals.

16. The method according to claim 14 wherein the impedance transducer comprises one or more selected from the group consisting of accelerometers, displacement transducers, load cells, and combinations thereof.

17. The method according to claim 1 wherein the device further comprises a means for determining the contact load.

18. The method according to claim 17 wherein the means for determining the contact load comprises a tissue contact pressure sensor.

19. The method according to claim 17 wherein the means for determining the contact load comprises a load cell.

20. The method according to claim 17 wherein the device further comprises a means for outputting that a desirable load has been achieved.

21. The method according to claim 20 wherein the means for outputting that a desirable load has been achieved comprises at least one LED.

22. The method of claim 1 wherein the contact load is between 10 N and 100 N.

23. The method according to claim 1 wherein the contact load is between 10 N and 20 N.

24. The method according to claim 1 further comprising repeating (a)-(c) at a different contact point.

25. The method according to claim 1 further comprising using a Fast Fourier transform to convert the force and tissue response measured in (c) into frequency domain data and using the frequency domain data to calculate mechanical transfer functions comprising accelerance, effective mass, mobility, impedance, compliance, or stiffness.

26. A method for testing an anatomical region, the method comprising:

(a) selecting operational parameters;

(b) engaging the anatomical region with a handheld device comprising an electromagnetic shaker, wherein a contact force is applied to the anatomical region by the handheld device yielding a contact pressure;

(c) simultaneously performing a frequency sweep over a range of frequencies based on a given set of operational parameters to generate mechanical vibrations within the same anatomical region while maintaining the contact pressure and collecting tissue response data with the handheld device at the same anatomical region in (b), the tissue response data including at least force and acceleration data from the mechanical vibrations; and (d) providing a response based on the tissue response data.

27. The method according to claim 26 wherein the force applied is from between 10 N and 100 N.

28. The method according to claim 26 wherein the contact pressure applies a force between 10 N and 20 N to the anatomical region.

29. The method according to claim 26 wherein the operational parameters are selected from the group consisting of anatomic site, age, sex, body weight, shoe size, and combinations thereof.

30. The method according to claim 29 wherein the operational information further comprises a file name.

31. The method according to claim 26 wherein the frequency sweep is between 20 Hz and 600 kHz.

32. The method according to claim 26 wherein the frequency sweep is between 800 Hz and 1.5 MHz.

33. The method according to claim 26 wherein providing a response based on the tissue response data comprises confirmation that the data collected was a valid sample.

34. The method according to claim 26 wherein providing a response based on the tissue response data comprises calculating one or more relative values based on comparative data from a database.

35. The method according to claim 26 wherein providing a response based on the tissue response data comprises
 (i) confirming that the data collected was a valid sample;
 (ii) calculating one or more raw values based on the data collected;
 (iii) comparing the raw values from (ii) to either:
  (1) one or more previous calculated raw values for a given patient from the same anatomic site or contralateral site, or
  (2) a database of similar values;
 (iv) determining a relative diagnosis based on the comparison in step (iii); and
 (v) communicating the relative diagnosis to a user.

36. The method according to claim 35 wherein the relative diagnosis comprises one or more forms selected from the group consisting of alpha-numeric characters, electronic data, graphs, pictures, video, charts, icons, sounds, and combinations thereof.

37. The method according to claim 26 further comprising repeating (a)-(d) at a different anatomical region.

38. The method according to claim 26 further comprising using a Fast Fourier transform to convert the tissue response data measured in (c) into frequency domain data and using the frequency domain data to calculate mechanical transfer functions comprising accelerance, effective mass, mobility, impedance, compliance, or stiffness.

* * * * *